United States Patent [19]
Marzorati

[11] Patent Number: 5,776,074
[45] Date of Patent: Jul. 7, 1998

[54] DYNAMIC SYSTEM OF SURVEY AND SELECTION OF TREATMENTS OF CELLULITE

[75] Inventor: Vittorio Marzorati, Bresso, Italy

[73] Assignee: I.P.S. International Products & Services S.r.l., San Donato Milanese, Italy

[21] Appl. No.: 662,670

[22] Filed: Jun. 14, 1996

[30] Foreign Application Priority Data

Jun. 15, 1995 [IT] Italy .................. MI95A1280

[51] Int. Cl.⁶ .................................. A61B 5/00
[52] U.S. Cl. .......................... 600/549; 128/898
[58] Field of Search ...................... 128/736, 664; 600/476–477, 549

[56] References Cited

U.S. PATENT DOCUMENTS

| | | | |
|---|---|---|---|
| 4,135,497 | 1/1979 | Meyers et al. | 128/736 |
| 4,138,889 | 2/1979 | Franschini | 128/736 |
| 4,175,543 | 11/1979 | Suzuki et al. | 128/736 |

*Primary Examiner*—Francis Jaworski
*Attorney, Agent, or Firm*—Dilworth & Barrese

[57] ABSTRACT

A system is described that allows to identify the area of the body affected by cellulite using microencapsulated liquid crystal thermodetectors that are elastic, flexible, or rigid which provide a thermal map of the surveyed area and to select the most appropriate treatments by a synoptic table that indicates, for each type of image displaced on the thermodetector, corresponding to a determined phase of the pathology and/or of the unaestheticism, the most adequate treatments for such a phase, subdivided in products, manipulations, physical exercises, and professional and medical systems.

20 Claims, 4 Drawing Sheets

DYNAMIC SYSTEM OF SURVEY AND SELECTION OF TREATMENTS OF CELLULITE

BACKGROUND OF THE INVENTION

The present invention regards a dynamic survey system of thermal signals by the cellulite that permits a) identification of the zones affected by cellulite b) to classify the cellulite in four thermographic phases, c) to choose the preventive and/or curative treatment most appropriate according to the detected phase, in a simple and utilizable manner not only by professional doctors, paramedics and cosmetologists, but also by the simple patient.

Cellulite is a pathology that affects most women in determined areas (thighs, glutes, abdominals, internal knee, shoulders, arms, etc.) causing progressive alterations of the microcirculatory system.

The cellulitic process has a very slow development. Generally it begins with a dilation of the capillaries (stagnant blood) followed by plasma emission (flooding of the tissues - edema). As time passes it fosters a natural process of defense for the fatty tissues, that are brought to the formation of the micronodule. The fusion of more micronodules finally produces the macronodule or cellulitic nodule, noticeable to palpation and painful to pressure.

These alterations cause variations of temperature: the areas with stagnant blood and edema are hotter, while the nodules are colder than the surrounding areas.

SUMMARY OF THE INVENTION

In order to understand if a region of the body is affected by cellulite, therefore, it is important to have recourse to a method that permits the detection of these modifications of temperature. Such method is the contact thermography with microencapsulated liquid crystals, technically easy and quickly executed, repeatable and above all harmless.

The system of the present invention utilizes this technique through a microencapsulated liquid crystal (E.L.C.) dynamic detector that, applied on the surface of the body being tested, assumes different colorations, providing a true and actual "thermal map" of that area.

BRIEF DESCRIPTION OF THE DRAWINGS

In order to execute the detection and to choose the most appropriate treatment the system of the present invention utilizes two fundamental articles, namely a dynamic thermodetector and a synoptic table, that come schematically illustrated in the attached sheets of drawings in which.

DETAILED DESCRIPTION OF THE PREFERRED EMBODIMENT

Figure 1A:
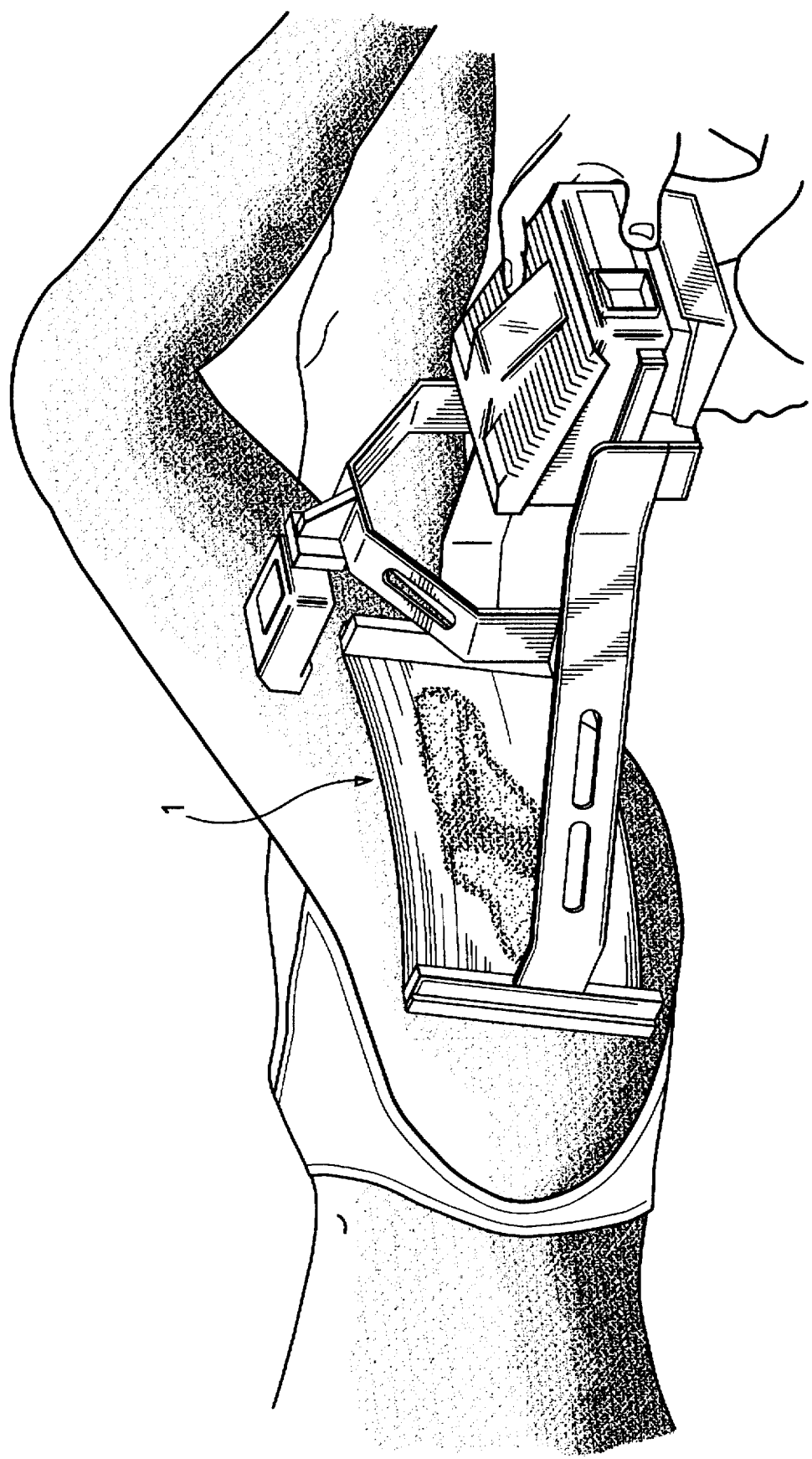
FIG. 1A shows a professional medical device 1 with photographic recording of the thermographic image.
Figure 1B:
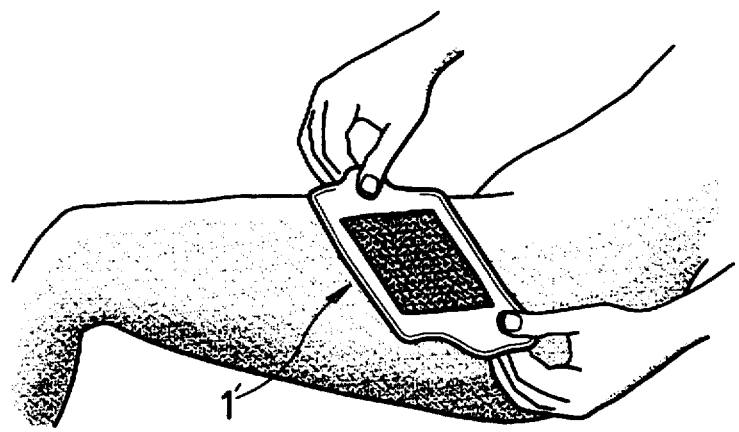
FIG. 1B shows the thermodetector 1' for personal application on an area of the body being tested.
Figure 1C:
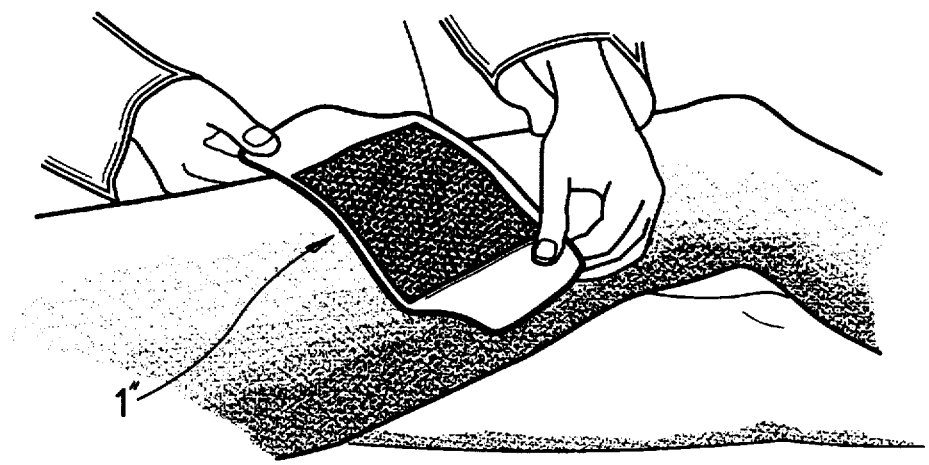
FIG. 1C shows a detector 1" for professional use by cosmetologists.

The dynamic thermodetectors shown in FIG. 1A, 1B, and 1C are of the type that are already normally used for other diagnostic inquiries, constituted from a flexible support on which a coating of microencapsulated liquid crystals for thermography is applied.

As is known, the liquid crystals have the property of changing color with the variation of temperature, and today high sensitivity liquid crystals are available that permit the displaying of temperature differentials up to 0.2° C. Each color of the liquid crystals represents a different temperature and appears according to a precise chromatic scale, from the lowest (brown-red) to the highest (green-violet-blue) temperatures.

In order to carry out in practice the detection, the thermodetector 1, 1',1" is applied on the skin of the areas to be examined. One waits for the stabilization of colors (about 10–20 seconds) before proceding to the interpretation of the image. The image that is formed on the thermodetector gives indications on the presence of thermal signals by the cellulite, permitting the accurate detection of the first cellulite signs (difficult to be detected by other means), the phase and the type of cellulite and the exact position of the cellutitic areas.

Figure 2:
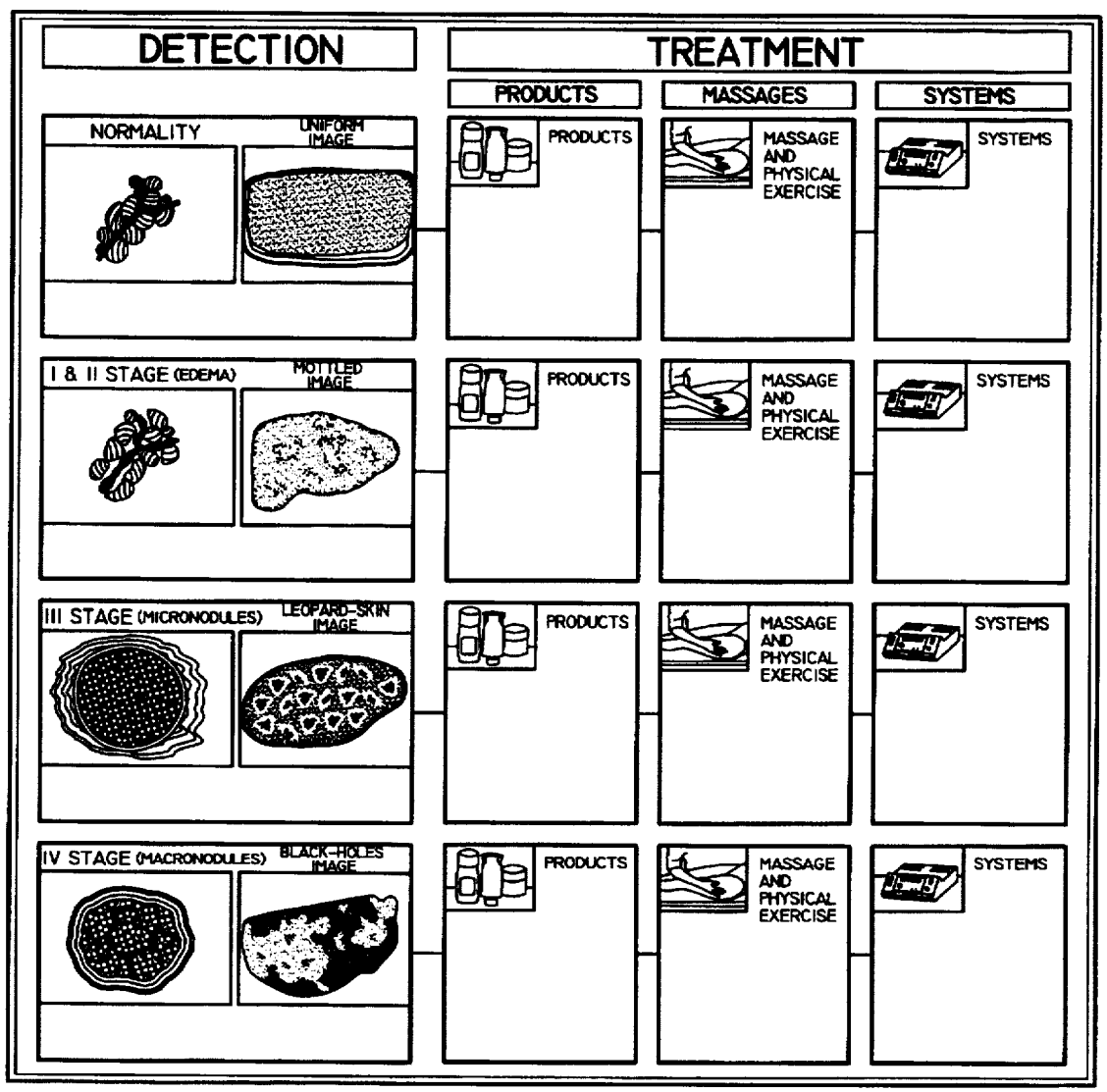
FIG. 2 shows the synoptic table in an embodiment for professional operators.
Figure 3:
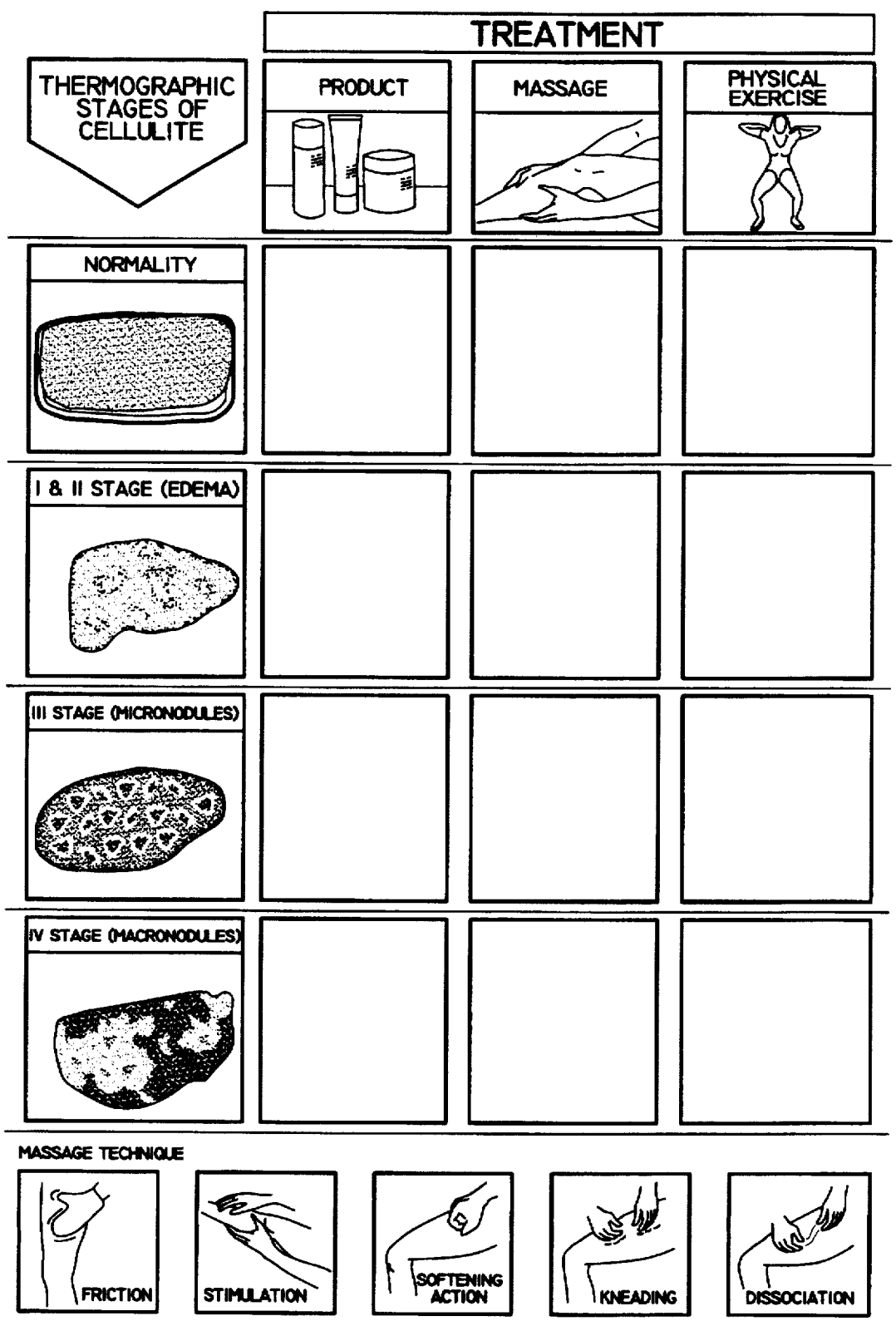
FIG. 3 shows the synoptic table in an embodiment for personal use.

Comparing the image on the thermodetector with that reported in the interpretive table showed in FIG. 2 and 3, it is possible to establish the presence or absence of the thermal signals of the cellulite, classified in four principal phases, thus being able to select the most effective treatment in respect of such phases. It must be pointed out that it is not so important to observe which colors appear on the thermodetector, as much as the image that is formed, and in particular it needs to be kept in mind that a uniform image indicates normality (absence of thermal signals of the cellulite) while a spotted image indicates the presence of thermal signals of the cellulite.

The synoptic table of FIG. 2 and 3 represent the main and innovative advantageous means of the system according to the present invention. This is divided into two sections, more particularly detection section, in which the characteristic images of normality and of the four principal phases of cellulite are illustrated, and the section showing, the treatments to be selected, paired to each image of the detection section.

The treatment section is then subdivided into three or more columns, that suggest respectively the products, the manipulations and the physical exercises, and in the tables for professional and medical use (see FIG. 2) also the mechanical, electronic, etc. systems being employed, corresponding to each surveyed phase. The table is finally able to be completed by illustrations (see FIG. 3) showing the massage techniques suggested in order to put into practice the suggestions of the manipulation treatment column.

Turning now to illustrate in greater detail the significance of the characteristic images that form on the thermodetector, the first or top box illustrates the thermographic uniform image; it displays a homogeneous coloration of one or two colors which appears prevalent on the thermodetector; an image of this type indicates a condition of normality or absence of the typical thermal signals of the cellulite.

The second box illustrates the hazy spotted images, corresponding to the I–II phase of the cellulite: this displays the presence of some big color spots with vague margins, often connected to each other; an image of this type is indicative of the first phases of cellulite, namely the edema.

The third box illustrates "the leopard skin image", corresponding to the III phase of the cellulite; this displays the presence of numerous sharp spots of different colors; an image of this type is indicative of thermal signals of cellulite with small nodules (micronodules).

The fourth and last box illustrates "the black spotted image", corresponding to the IV phase of the cellulite; this displays the presence of sharp colored spots near brown/black areas; this is the thermal sign of an advanced phase of the cellulite, characterized by the presence of large nodules (macronodules) with little or no vascularization.

The thermographic test may be repeated for an unlinmited number of times, so as to check the advancement of the pathology. The test is clearly not invasive and is lacking contra-indications.

Therefore it results that, comparing the formed image on the thermodetector with the illustrative images of the table and checking the columns of the treatment section corresponding to the equivalent image to that of the thermodetector, one has the immediate response to the relevant question and the most appropriate suggestion for the following treatments.

The specific brand of the products will be able to be suggested by the trusted professional, whether it is a physician, pharmacist, therapist or cosmetologist. In any case, the products that are applied alone, mixed or in combination, using the massage techniques advised, according to the cellulite phase detected, belong in a non-limiting manner to the following specialty categories; Decongestant products in order to reduce the intensity of the edema and to help the reabsorption across all the lymphatic vessels. Moisturizing products in order to restore hydration and elasticity of the skin. Invigorating products and lipolytics in order to assist in the reduction of volume of the adipocytes and in order to intensity the invigoration of the muscular fibers. Toning-up products in order to maintain the elasticity of the skin and to prevent the anti-aesthetic effects that may occur in view of loss of weight or reduction of measures (for example reduction of the circumference of the leg because of adiposity reduction and the absorption of the edema). Vasotonic products in order to assist in the oxygenation of the tissues and to augment the volume of the capillaries and the speed of the blood supply.

As to the massage, which is the principal component of an effective treatment of the cellulite, the fundamental techniques to be followed, indicated in a non-limiting manner also schematically at the bottom of the table, are the rub down, the support to the microcirculation with movement of the hands in the sense of the venous flow, the softening action by means of spotting, the kneading by means of flight rhythmic compression of the skin, the disassociation through traction in opposite directions of an epidermic fold, the drainage massage.

As far as the physical exercises are concerned, these are mostly those followed in order to gain back the figure, with warm-up movements and stretching, specific physical exercises for the various body parts such as thighs, calves, arms, shoulders, sides, glutes, and pectorals.

Finally as to the medical systems to be used, one can mention in a non-limiting manner the mechanical or electronic sequential lymph drainage pressure therapy, electrolypolysis (by needles or plates), localized ultrasounds on the edematous and/or nodular areas, balneotherapy at various temperatures, localized mesotherapy with vaso-trophic, antiedema, lipolytic and/or fibrolytic products according to the specific case, passive warm-ups and ionophoresis penetration of the products and of the active substances.

From the foregoing it is to be understood that the system of the present invention represents the method of detection and selection of the most complete treatment that responds to the greatest part of the problems caused by the complete cellulitic pathology, and it has also to be pointed out that the layout of the sections on the illustrated table displayed in the attached drawing is simply exemplificative and therefore variations may be resorted to it without altering the fundamental concept of accompanying thermographic images with the advised treatments for the corresponding cellulitic phases.

I claim:

1. Dynamic system of survey and selection of treatment of cellulite, including an elastic, flexible or rigid thermodetector of microencapsulated liquid crystals disposed to assume different colorations when applied to a surface of a body being examined and thereby providing a thermal map of the examined area, and a synoptic table illustrating each type of image that can be displayed on the thermal detector together with a selection of advised treatments for the type of cellulitic pathology indicated by such an image.

2. System according to claim 1, wherein the thermodetector includes a layer of high sensitivity microencapsulated liquid crystals that allows for displaying temperature differentials up to 0.2° C.

3. System according to claim 1, wherein the synoptic table is divided into two sections, a first one of which being a detection section which illustrates characteristic images of normality and four principal phases of cellulite, and the other of which being a treatment section illustrating treatments to be chosen and joined to each image of the detection section.

4. System according to claim 3, wherein the treatment section is further subdivided into three or more columns, that provide in a non-limiting manner, products which can be used, manipulations and physical exercises which can be carried out corresponding to each detected phase.

5. System according to claim 4, wherein the treatment section further contains a column illustrating a medical-aesthetic system which can be employed to treat cellulite based upon the detected phase.

6. A system according to claim 5, wherein the medical system to be utilized includes mechanical or electronic sequential lymph drainage pressure therapy, electrolypolysis, ultrasound, balneotherapy, localized mesotherapy, passive warm-ups, and ionophoresis penetration.

7. System according to claim 3, wherein the table also contains a series of illustrations displaying advised massage techniques in order to put into practice the manipulation treatments.

8. System according to claim 1, wherein the thermodetector is disposed to provide indication on the presence of thermal signals by cellulite by providing a shaped image of colorations produced thereon.

9. System according to claim 8, wherein the synoptic table comprises, in a first column, four boxes illustrating various thermographic uniform images as follows;

(i) a first or top box displaying homogeneous coloration of one or two colors indicating condition of normality or absence of thermal signals in denoting cellulite presence, (ii) a second box illustrating hazy spotted images corresponding to indication of I-II phase cellulite condition;

(iii) a third box illustrating an image corresponding to presence of III phase cellulite condition; and (iv) a fourth or bottom box illustrating an image corresponding to indication of IV phase cellulite condition.

10. System according to claim 8, wherein the synoptic table additionally contains three additional columns, each of said columns being respectively devoted to products, massages and physical exercise for addressing the various stages of cellulitic presence indicated by adjacent thermographic images in the first column.

11. System according to claim 10, wherein the first additional column illustrates at least one of decongestant products, moisturizing products, invigorating products, toning products and vasotonic products that can be applied to treat the requisite cellulitic stage indication, the second additional column illustrates massage technique to be applied and the third additional column illustrates physical exercise to be applied including warming-up movements and stretching, in addition to specific physical exercises for various body parts.

12. A method for diagnosing and treating presence of cellulite on a body, comprising the steps of:

applying to a surface of the body, an elastic, flexible or rigid thermodetector containing microencapsulated liquid crystals that change color with variation in temperature, each color of the liquid crystals representing a different temperature according to a precise chromatic scale, allowing the thermodetector to remain against the body surface for a period of time, whereby the microencapsulated liquid crystals change colors and display a shaped image on the thermodetector, comparing the shaped image thus displayed on the thermodetector with images formed upon an interpretive, synoptic table indicating existence of cellulite based upon the shape of the image thus displayed on the thermodetector, and if presence of cellulite is indicated, proceeding with any appropriate treatment based upon a selection of advised treatments for type of cellulite pathology indicated by the shape of the image formed on the table.

13. The method of claim 12, comprising the additional step of recording the displayed shaped image on a suitable medium.

14. The method of claim 12, wherein appropriate treatment is immediately proceeded with upon indication of presence of cellulite.

15. The method of claim 12, wherein temperature differentials up to 0.2° C. are displayed upon the thermodetector containing a layer of high sensitivity microencapsulated liquid crystals.

16. The method of claim 12, comprising the additional step of dividing the synoptic table into two sections, a first section illustrating characteristic images of normality and four principal phases of cellulite, and a second section illustrating treatments to be chosen depending upon each image shown in the first adjacent section.

17. The method of claim 16, comprising the additional step of dividing the second treatment section of the synoptic table into three or more columns to provide, in a non-limiting treatment manner, products which can be used, manipulations and physical exercises which can be carried out, corresponding to the respective phase of cellulitic indication adjacently shown in the first section.

18. The method of claim 17, wherein the treatment section of the synoptic table further illustrates medical-aesthetic systems which can be employed in the treatment of the adjacently illustrated cellulitic phase indication.

19. The method of claim 16, comprising the additional step of arranging the synoptic table to contain a series of illustrations displaying recommended massage techniques in order to put into practice the requisite treatments.

20. The method of claim 16, comprising the additional step of providing a column in the first section containing four boxes illustrating various thermographic uniform images as follows:

(i) a first or top box displaying homogeneous coloration of one or two colors indicating condition of normality or absence of thermal signals in denoting cellulite presence, (ii) a second box illustrating hazy spotted images corresponding to indication of I–II phase cellulite condition;

(iii) a third box illustrating an image corresponding to presence of III phase cellulite condition; and (iv) a fourth or bottom box illustrating an image corresponding to indication of IV phase cellulite condition.

* * * * *